US011253596B2

(12) United States Patent
Gschneidner et al.

(10) Patent No.: US 11,253,596 B2
(45) Date of Patent: *Feb. 22, 2022

(54) PHENYLALKYLCARBOXYLIC ACID DELIVERY AGENTS

(71) Applicant: Emisphere Technologies, Inc., Roseland, NJ (US)

(72) Inventors: David Gschneidner, Roseland, NJ (US); Stephen V. Pusztay, Orchard Park, NY (US)

(73) Assignee: NOVO NORDISK NORTH AMERICA OPERATIONS A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/597,053

(22) Filed: Oct. 9, 2019

(65) Prior Publication Data

US 2020/0405863 A1  Dec. 31, 2020

Related U.S. Application Data

(63) Continuation of application No. 15/198,392, filed on Jun. 30, 2016, now Pat. No. 10,456,472, which is a continuation of application No. 13/474,491, filed on May 17, 2012, now abandoned, which is a continuation of application No. 12/522,464, filed as application No. PCT/US2008/053429 on Feb. 8, 2008, now abandoned.

(60) Provisional application No. 60/888,927, filed on Feb. 8, 2007.

(51) Int. Cl.
*A61K 47/12* (2006.01)
*A61K 38/28* (2006.01)
*A61K 38/26* (2006.01)
*A61K 9/00* (2006.01)
*A61K 9/20* (2006.01)
*A61K 45/06* (2006.01)

(52) U.S. Cl.
CPC ............ *A61K 47/12* (2013.01); *A61K 9/0095* (2013.01); *A61K 9/2013* (2013.01); *A61K 38/26* (2013.01); *A61K 38/28* (2013.01); *A61K 45/06* (2013.01)

(58) Field of Classification Search
CPC ........ A61K 38/26; A61K 38/28; A61K 45/06; A61K 47/12; A61P 19/10; A61P 3/10; A61P 31/12; A61P 31/18; A61P 35/00; A61P 5/48; A61P 7/06; A61P 9/08
See application file for complete search history.

(56) References Cited

U.S. PATENT DOCUMENTS

| 5,401,516 | A | 3/1995 | Milstein et al. |
| 5,443,841 | A | 8/1995 | Milstein et al. |
| 5,541,155 | A | 7/1996 | Leone-Bay et al. |
| 5,629,020 | A | 5/1997 | Leone-Bay et al. |
| 5,643,957 | A | 7/1997 | Leone-Bay et al. |
| 5,766,633 | A | 6/1998 | Milstein et al. |
| RE35,862 | E | 7/1998 | Steiner et al. |
| 5,776,888 | A | 7/1998 | Leone-Bay et al. |
| 5,866,536 | A | 2/1999 | Leone-Bay et al. |
| 6,656,922 | B2 | 12/2003 | Byun et al. |
| 8,273,794 | B2 | 9/2012 | Gomez-Orellana et al. |
| 8,383,852 | B2 | 2/2013 | Tang et al. |
| 10,456,472 | B2 * | 10/2019 | Gschneidner .............. A61P 9/08 |
| 2003/0203851 | A1 | 10/2003 | Gyorkos et al. |

FOREIGN PATENT DOCUMENTS

| WO | WO-9612473 A1 | 5/1996 |
| WO | WO-9612475 A1 | 5/1996 |
| WO | WO-9834632 A1 | 8/1998 |
| WO | WO-9961481 A1 | 12/1999 |
| WO | WO-2000-22909 | 4/2000 |
| WO | WO-200040203 A2 | 7/2000 |
| WO | WO-0132596 A1 | 5/2001 |
| WO | WO-0220466 A1 | 3/2002 |

OTHER PUBLICATIONS

Levrand et al., Light induced control release of alkyl phenyl ketones, Photochemical & Biological Sciences (2002), 1(11), 907-191, CAPLUS [online] Columbus, OH, USA Chemical Abstracts [retreived on May 24, 2006].
Fujita, Studies on w-Cyclic Fatty Acids III. Synthesis of some Hydroxyaroyl-and Hydroxyaryl fatty acids, Yakugaku Zasshi, 76/1, pp. 37-40, 1956, STN accession # 50:69243.
Treibs, "Synthesen mit Dicarbonsauren VI. Mittel.: Die Fries'sche Verschiebung at Estem von Dicarbon sauren", Chemische Berichte, 87/3, pp. 345-349, 1954, STN accession #49:23600.
International Search Report issued in PCT/US08/53429 dated Sep. 25, 2008.
STN Registry Jan. 27, 2006 CAS RN=4521-28-2 et al., Apr. 20, 2012.

* cited by examiner

*Primary Examiner* — My-Chau T. Tran
(74) *Attorney, Agent, or Firm* — Blank Rome LLP

(57) ABSTRACT

The present invention provides phenylalkylcarboxylic acid compounds and compositions containing such compounds which facilitate the delivery of biologically active agents.

20 Claims, No Drawings

PHENYLALKYLCARBOXYLIC ACID DELIVERY AGENTS

This application is a continuation of U.S. patent application Ser. No. 15/198,392, filed Jun. 30, 2016, which is a continuation of U.S. patent application Ser. No. 13/474,491, filed May 17, 2012, now abandoned, which is a continuation of U.S. patent application Ser. No. 12/522,464, filed Oct. 14, 2009, now abandoned, which is the U.S. national phase of International Application No. PCT/US08/53429, filed Feb. 8, 2008, which claims the benefit of U.S. Provisional Application No. 60/888,927, filed Feb. 8, 2007.

FIELD OF THE INVENTION

The present invention relates phenylalkylcarboxylic acid compounds and compositions which facilitate the delivery of active agents.

BACKGROUND OF THE INVENTION

Conventional means for delivering active agents are often severely limited by biological, chemical and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766, 633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides phenylalkylcarboxylic acid compounds and compositions which facilitate the delivery of active agents (e.g. biologically active agents). Delivery agent compounds of the present invention include those having the formula:

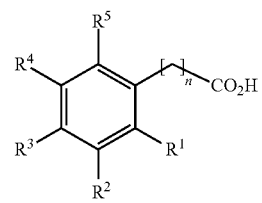

Formula I and pharmaceutically acceptable salts thereof, wherein
n is 1-12,
and $R^1$-$R^5$ are independently hydrogen, $C_1$-$C_6$ alkyl, $C_2$-$C_4$ alkenyl, halogen, $C_1$-$C_4$ alkyloxy, hydroxyl, $C_6$-$C_{14}$ aryloxy, or $C_1$-$C_6$ alkylhalo (e.g. $C_1$ alkylhalo) group.

According to one embodiment, n ranges from 1 to 9. For example, n may be 1-9, 2-9, 3-9, 4-9, 5-9, 6-9, 7-9, 8-9, 1-8, 2-8, 3-8, 4-8, 5-8, 6-8, 7-8, 1-7, 2-7, 3-7, 4-7, 5-7, 6-7, 1-6, 2-6, 3-6, 4-6, 5-6, 1-5, 2-5, 3-5, 4-5, 1-4, 2-4, 3-4, 1-3, 2-3 or 1-2.

According to another embodiment, at least one of $R^1$ to $R^5$ is methyl, methoxy, hydroxy or halogen group (e.g., Cl or F).

Mixtures of these delivery agent compounds may also be used.

The invention also provides a pharmaceutical composition comprising at least one delivery agent compound of the present invention, and at least one active agent (e.g. a biologically active agent). When administered with an active agent, delivery agents of the present application improve the bioavailability of the active agent compared to administration of the active agent without the delivery agent compound.

Also provided is a dosage unit form comprising a pharmaceutical composition of the present invention. The dosage unit form may be in the form of a liquid or a solid, such as a tablet, capsule or particle, including a powder or sachet.

Another embodiment is a method for administering an active agent to an animal, particularly an animal in need of the active agent, by administering a pharmaceutical composition comprising at least one of delivery agent compound of the present invention and the active agent to the animal. Preferred routes of administration include the oral and intracolonic routes, particularly the oral route.

Yet another embodiment of the present invention is a method of treating a disease or for achieving a desired physiological effect in an animal (e.g. a human) by administering to the animal the pharmaceutical composition of the present invention.

Yet another embodiment of the present invention is a method of preparing a pharmaceutical composition of the present invention by mixing at least one delivery agent compound of the present invention, and at least one active agent.

Yet another embodiment of the present invention is a method of increasing the bioavailability (e.g., the oral bioavailability) of a pharmaceutical composition containing an active agent (e.g., abiologically active agent) comprising adding a delivery agent compound of the present invention to the pharmaceutical composition.

DETAILED DESCRIPTION OF THE INVENTION

Definitions

The term "alkyl" refers to a straight-chained, branched, or substituted monovalent aliphatic hydrocarbon group containing no double or triple carbon-carbon bonds. Examples of alkyl group include, but are not limited to, methyl, ethyl, n-propyl, 1-methylethyl (isopropyl), n-butyl, n-pentyl, and 1-dimethylethyl (t-butyl).

The term "alkenyl" refers to a straight-chained, branched, or substituted monovalent aliphatic hydrocarbon group containing at least one carbon-carbon double bond. Examples of alkenyl groups include, but are not limited to, ethenyl, 1-propenyl, 2-propenyl (allyl), iso-propenyl, 2-methyl-1-propenyl, 1-butenyl, and 2-butenyl.

The term "alkylene" refers to a straight-chained, branched or substituted divalent aliphatic hydrocarbon group containing no double or triple bonds.

The term "alkyloxy" refers to an alkyl group attached via an oxygen linkage to the rest of the molecule. Examples of alkyloxy groups include, but are not limited to, —$OCH_3$, and —$OC_2H_5$ groups.

The term "aryl" refers to an monovalent $C_6$-$C_{14}$ aromatic group, i.e. a monovalent group having one or more unsaturated carbon rings. Examples of aryl groups, include, but are not limited to, phenyl, naphthyl, tetrahydronapthyl, indanyl, and biphenyl.

The term "alkyl(arylene)" refers to a divalent group containing an aromatic group with an alkyl group before and/or after the aromatic group.

The term "aryloxy" refers to an $C_6$-$C_{14}$ aryl group attached via an oxygen linkage to the rest of the molecule, such as —$OC_6H_5$.

The term "insulin" includes recombinant forms of insulin (e.g. recombinant human insulin), analogs of insulin lispro or Humalog®) as well as regular forms of insulin of human or other animal origin.

The term "heparin" includes unfractionated heparin, low molecular weight heparin, very low molecular weight heparin, of recombinant, human, or other animal origin.

The term "LHRH" or "luteinizing hormone-releasing hormone" refers to a hormone produced by the hypothalamus that signals the anterior pituitary gland to begin secreting luteinizing hormone and follicle-stimulating hormone.

The term "rhGH" refers to recombinant human growth hormone.

The term "caspofungin" or "caspofungin acetate" refers to a water-soluble, semisynthetic lipopeptide derived from the fungus, Glarea lozoyensis, that has activity against Aspergillus and Candida species. Caspofugin acetate (Cancidas®) has been approved by the FDA and is indicated for the treatment of invasive aspergillosis in patients who are refractory to or intolerant of other antifungal agents.

Unless otherwise specified, the term "substituted" as used herein refers to substitution with any one or any combination of the following substituents: hydroxy, $C_1$-$C_6$ alkyl, including methyl, ethyl, propyl, isopropyl, normal or iso-butyl; $C_2$-$C_4$ alkenyl, $C_1$-$C_4$ alkyloxy, aryl, halo, alkylhalo, or aryloxy groups.

The term "about" means generally means within 10%, preferably within 5%, and more preferably within 1% of a given range.

The term "short stature" refers to a subject with a size (e.g. a height) that is significantly below what is considered normal. Growth hormone, e.g., human growth hormone, is indicated for short stature.

Delivery Agent Compounds

Delivery agent compounds of the present invention include those compounds represented by Formula I below, and pharmaceutically acceptable salts thereof:

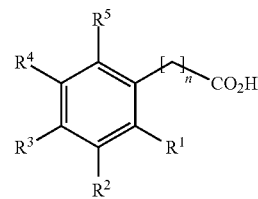

Formula I wherein n is 1-12; and $R_1$-$R_5$ are independently hydrogen, $C_1$-$C_6$ alkyl, $C_2$-$C_4$ alkenyl, halo, $C_1$-$C_4$ alkyloxy, hydroxyl, $C_6$-$C_{14}$ aryloxy, or $C_1$-$C_6$ alkylhalo group (e.g. $C_1$ alkylhalo).

In various embodiments, n may be 1-9, 2-9, 3-9, 4-9, 5-9, 6-9, 7-9, 8-9, 1-8, 2-8, 3-8, 4-8, 5-8, 6-8, 7-8, 1-7, 2-7, 3-7, 4-7, 5-7, 6-7, 1-6, 2-6, 3-6, 4-6, 5-6, 1- 5, 2-5, 3-5, 4-5, 1-4, 2-4, 3-4, 1-3, 2-3 or 1-2.

In another embodiment of the present invention, delivery agent compounds of the present invention include those compounds represented by Formula I above in which at least one of $R_1$-$R_5$ is a methyl, methoxy, alkyloxy, hydroxy or halogen group. In a preferred embodiment, delivery agent compounds include those in which n is defined as in the preceding paragraph and at least one of $R_1$-$R_5$ is a methyl, methoxy, alkyloxy, hydroxy, or halogen group.

In one embodiment of the present invention, delivery agent compounds are selected from Formula I above, in which at least one of $R_1$-$R_5$ is a methyl group. In another embodiment, delivery agent compounds are selected from Formula I above in which at least one of $R_1$-$R_5$ is a methoxy group. In another embodiment, delivery agent compounds are selected from Formula I above in which at least one of $R_1$-$R_5$ is a hydroxy group. In another embodiment, delivery agent compounds are selected from Formula I above in which at least one of $R_1$-$R_5$ is an aryloxy group. In another embodiment, delivery agent compounds are selected from Formula I above in which at least one of $R_1$-$R_5$ is an alkyloxy group. In another embodiment, delivery agent compounds are selected from Formula I above in which at least one of $R_1$-$R_5$ is a $C_1$ alkylhalo group. In another embodiment, delivery agent compounds are selected from Formula I above in which at least one of $R_1$-$R_5$ is a halogen, preferably at least one of $R_1$-$R_5$ is a chlorine atom or at least one of $R_1$-$R_5$ is a fluorine atom.

In one embodiment of the present invention, the compounds listed in Table 1 are excluded as delivery agents of Formula I. However, in various embodiments these compounds may be included in compositions that further include an active agent (e.g., a biologically active agent).

The delivery agent compounds may be in the form of the free base or pharmaceutically acceptable salts thereof, such as pharmaceutically acceptable acid addition salts. Suitable salts include, but are not limited to, organic and inorganic salts, for example ammonium, acetate salt, citrate salt, halide (preferably hydrochloride), hydroxide, sulfate, nitrate, phosphate, alkyloxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O)—, —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly (propylene); polypropylene glycol; polyethyleneglycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment of the present invention, the molecular weight of the polymer ranges from about 200 to about 600 daltons and more preferably ranges from about 300 to about 550 daltons.

Non-limiting examples of delivery agent compounds of Formula I include those shown below and pharmaceutically acceptable salts thereof:

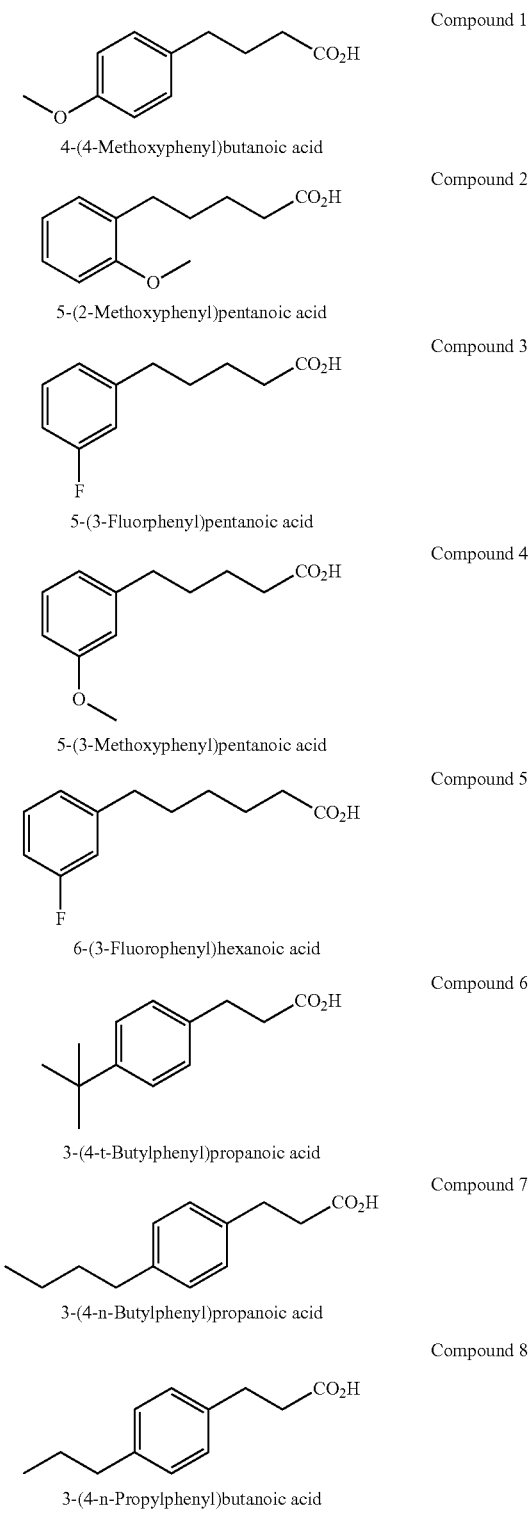

Compound 1
4-(4-Methoxyphenyl)butanoic acid

Compound 2
5-(2-Methoxyphenyl)pentanoic acid

Compound 3
5-(3-Fluorophenyl)pentanoic acid

Compound 4
5-(3-Methoxyphenyl)pentanoic acid

Compound 5
6-(3-Fluorophenyl)hexanoic acid

Compound 6
3-(4-t-Butylphenyl)propanoic acid

Compound 7
3-(4-n-Butylphenyl)propanoic acid

Compound 8
3-(4-n-Propylphenyl)butanoic acid

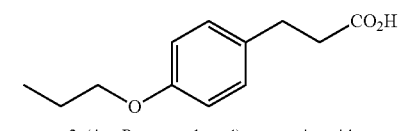

3-(4-n-Propoxyphenyl)propanoic acid

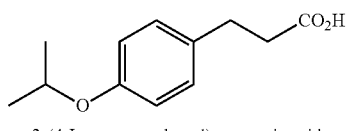

3-(4-Isopropoxyphenyl)propanoic acid

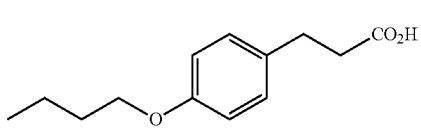

3-(4-n-Butylphenyl)propanoic acid

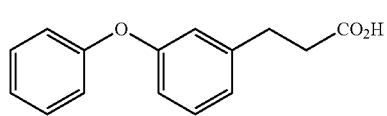

3-(3-Phenoxyphenyl)propanoic acid

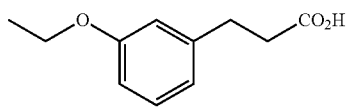

3-(3-Ethoxyphenyl)propanoic acid

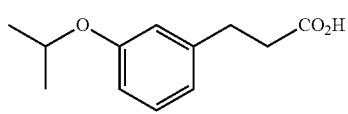

3-(3-Isopropoxyphenyl)propanoic acid

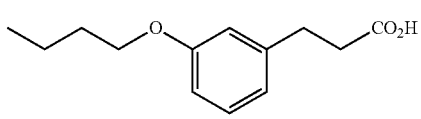

3-(3-n-Butoxyphenyl)propanoic acid

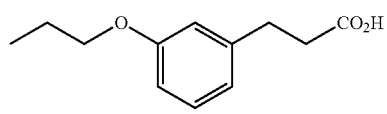

3-(3-n-Propoxyphenyl)propanoic acid

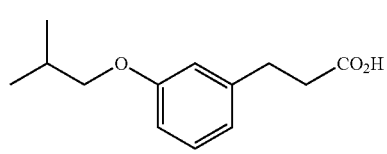

3-(3-Isobutoxyphenyl)propanoic acid

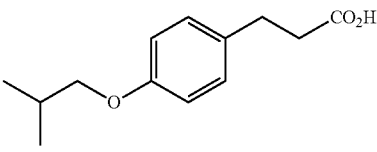

3-(4-Isobutoxyphenyl)propanoic acid

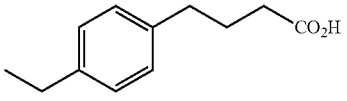

4-(4-Ethylphenyl)butanoic acid

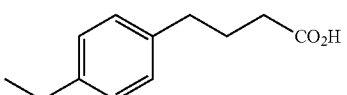

4-(4-Isopropylphenyl)butanoic acid

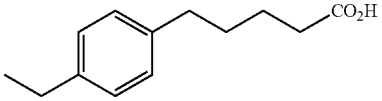

5-(4-Ethylphenyl)pentanoic acid

Compounds 22-74 (Table 1) were purchased from commercially available sources for utilization as delivery agents.

TABLE 1

Commercial compounds utilized as delivery agents

| Delivery Agent Compound # | Purchased from | Chemical name |
|---|---|---|
| 22 | Sigma-Aldrich (St. Louis, MO) | Benzeneacetic acid |
| 23 | Johnson Matthey (London, UK) | 8-Phenyloctanoic acid |
| 24 | Lancaster (Windham, NH) | 10-Phenyldecoic acid |
| 25 | Lancaster | 4-(4-Methylphenyl)butanoic acid |
| 26 | Lancaster | 3-(3-Hydroxyphenyl)propanoic acid |
| 27 | Sigma-Aldrich | 3-(p-Hydroxyphenyl)propanoic acid |
| 28 | Sigma-Aldrich | 5-Phenylpentanoic acid |
| 29 | Sigma-Aldrich | 6-Phenylhexanoic acid |
| 30 | Matrix Scientific (Columbia, SC) | 2-Phenoxyphenylethanoic acid |
| 31 | Matrix Scientific | 4-Phenoxyphenylethanoic acid |
| 32 | Lancaster | 7-Phenylheptanoic acid |
| 33 | Johnson Matthey | 3-(4-Methylphenyl)propanoic acid |
| 34 | Johnson Matthey | 3-(3,4-Dihydroxyphenyl)propanoic acid |
| 35 | Johnson Matthey | 3-(2-Hydroxyphenyl)propanoic acid |
| 36 | Sigma-Aldrich | 3-[4-(Trifluoromethyl)phenyl]propanoic acid |
| 37 | Sigma-Aldrich | 3-[2,5-Bis(Trifluoromethyl)phenyl]propanoic acid |
| 38 | Trans World Chemicals (Rockville, MD) | 3-(2-Fluorophenyl)propanoic acid |
| 39 | Trans World Chemicals | 3-(3-Fluorophenyl)propanoic acid |
| 40 | Sigma-Aldrich | 3-(3,4-Difluorophenyl)propanoic acid |
| 41 | Trans World Chemicals | 3-(4-Fluorophenyl)propanoic acid |
| 42 | Trans World Chemicals | 3-(2-Methylphenyl)propanoic acid |
| 43 | Matrix Scientific | 2-(3-Phenoxyphenyl)ethanoic acid |
| 44 | Lancaster | 4-Phenylbutanoic acid |

TABLE 1-continued

Commercial compounds utilized as delivery agents

| Delivery Agent Compound # | Purchased from | Chemical name |
|---|---|---|
| 45 | Trans World Chemicals | 3-(2,4-Dichlorophenyl) propanoic acid |
| 46 | Trans World Chemicals | 3-(2,4-Dimethylphenyl) propanoic acid |
| 47 | Trans World Chemicals | 3-(2-Chlorophenyl) propanoic acid |
| 48 | Trans World Chemicals | 3-(3,4-Dichlorophenyl) propanoic acid |
| 49 | Trans World Chemicals | 3-(3,5-Dimethoxyphenyl)propanoic acid |
| 50 | Trans World Chemicals | 3-(4-Iodophenyl)propanoic acid |
| 51 | Trans World Chemicals | 3-(3-Methylphenyl) propanoic acid |
| 52 | Trans World Chemicals | 3-(4-Chlorophenyl) propanoic acid |
| 53 | Trans World Chemicals | 3-(4-Ethylphenyl) propanoic acid |
| 54 | Trans World Chemicals | 3-(3-Iodophenyl) propanoic acid |
| 55 | Trans World Chemicals | 3-(4-Isopropylphenyl) propanoic acid |
| 56 | Sigma-Aldrich | 3-(3-Chloro-4-methoxyphenyl) propanoic acid |
| 57 | Trans World Chemicals | 3-(3-Bromophenyl) propanoic acid |
| 58 | Trans World Chemicals | 3-(3,4-Dimethylphenyl) propanoic acid |
| 59 | Trans World Chemicals | 3-(3-Chlorophenyl) propanoic acid |
| 60 | Trans World Chemicals | 3-(2-Bromophenyl) propanoic acid |
| 61 | Trans World Chemicals | 3-(4-Bromophenyl)propanoic acid |
| 62 | Trans World Chemicals | 3-(2-Methoxyphenyl)propanoic acid |
| 64 | Sigma-Aldrich | 3-(4-Methoxyphenyl)propanoic acid |
| 65 | Sigma-Aldrich | 3-(2,3-Dimethoxyphenyl)propanoic acid |
| 66 | Sigma-Aldrich | 3-(3,4-Dimethoxyphenyl)propanoic acid |
| 67 | Sigma-Aldrich | 4-(p-Iodophenyl)butanoic acid |
| 68 | Sigma-Aldrich | 3-(3,4,5-Trimethoxyphenyl)propanoic acid |
| 69 | Sigma-Aldrich | 4-(3,4-Dimethoxyphenyl)butanoic acid |
| 70 | Sigma-Aldrich | 3-[3,5-Bis(Trifluoromethyl)phenyl]propanoic acid |
| 71 | Sigma-Aldrich | 3-(2,4-Dimethoxyphenyl)propanoic acid |
| 72 | Sigma-Aldrich | 3-(2,5-Dimethoxyphenyl)propanoic acid |
| 73 | Oakwood Products Inc. (West Columbia, SC) | 5-(4-Fluorophenyl)pentanoic acid |
| 74 | Trans World Chemicals | 3-(4-Ethoxyphenyl)propanoic acid |

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α-interferon (e.g., interferon alfacon-1 (available as Infergen® from InterMune, Inc. of Brisbane, Calif.)), β-interferon and γ-interferon; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as sumatriptan, almotriptan, naratriptan, rizatriptan, frovatriptan, eletriptan, BIBN-4096BS and other calcitonin gene-related proteins antagonists; glucagon-like peptide 1 (GLP-1); Argatroban; glucagon; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The pharmaceutical composition of the present invention comprises one or more delivery agent compounds of the present invention, and one or more active agents (e.g., biologically active agents). In one embodiment, one or more of the delivery agent compounds, or salts of these compounds, may be used as a delivery agent by mixing delivery agent compounds with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include, but are not limited to, polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process. Alternatively, the delivery agent compound and active agent can be separately administered in sequential fashion.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitors.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

Generally, the amount of delivery agent compound in the composition is an amount effective to facilitate delivery of the active agent. The total amount of active agent and delivery agent to be used can be determined by methods known to the skilled artisan. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects. Generally, the weight ratio of delivery agent to active agent ranges from about 1000:1 or 800:1 to about 10:1 or 1:10, and preferably ranges from about 400:1 or 200:1 to about 100:1 or 25:1. Other ranges are contemplated to be within acceptable ranges for delivery of some active compounds, such as from about 100:1 or 50:1 to about 5:1 or 2.5:1, or from about 60:1 or 30:1 to about 1:1 or 0.5:1. Such ranges and ratios can be determined by one skilled in the art.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the phenylalkyl carboxylic acid compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as any one of the diseases or conditions listed in the table below, in an animal by administering the composition of the present invention. Preferably, an effective amount of the composition for the treatment or prevention of the desired disease or for achieving the desired physiological effect is administered. Specific indications for active agents can be found in the The Physicians' Desk Reference ($58^{th}$ Ed., 2004, Medical Economics Company, Inc., Montvale, N.J.), and Fauci, A S, et. al., Harrison's Principles of Internal Medicine ($14^{th}$ Ed., 1998, McGraw-Hill Health Professions Division, New York. Both of these references are herein incorporated by reference in their entirety. The active agents in the table below include their analogs, fragments, mimetics, and polyethylene glycol-modified derivatives (e.g., the PEGylated derivative of granulocyte colony stimulating factor sold as Neulasta®).

TABLE 2

Active agent utilization

| Active Agent | Disease and Physiological Effect |
|---|---|
| Growth hormones (including human recombinant growth hormone and growth-hormone releasing factors and its analogs) | Growth disorders |

TABLE 2-continued

Active agent utilization

| Active Agent | Disease and Physiological Effect |
| --- | --- |
| Interferons, including α, β and γ | Viral infection, including chronic cancer, hepatitis, and multiple sclerosis |
| Interleukins (e.g. Interleukin-1; interleukin-2) | Viral infection; cancer; cell mediated immunity; and transplant rejection; |
| Insulin; Insulin-like growth factor IGF-1 | Diabetes |
| Immune Globulins, such as IVIg | smallpox, rabies, and diphtheria, Alzheimer's Disease; Primary immunodeficiencies; Acute Guillain-Barré syndrome; Chronic idiopathic demyelinating polyneuropathy (CIDP); Myasthenia gravis, polymyositis, and dermatomyositis; neonatal immune thrombocytopenia, heparin-induced thrombocytopenia, and antiphospholipid antibody syndrome: Posttransfusion purpura. |
| Heparin | Treatment and Prevention of Thrombosis, including Deep Vein Thrombosis; prevention of blood coagulation |
| Calcitonin | Osteoporosis; diseases of the bone; bone pain; analgesic (including pain associated with osteoporosis or cancer) |
| Erythropoietin, Pegylated erythropoietin. | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in connection with Alzheimer's disease,Type II diabetes, and other amyloid-based diseases |
| Monoclonal antibodies | To prevent graft rejection; cancer; used in assays to detect diseases |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; Leutinizing Hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) and their Pegylated forms | shorten the duration of chemotherapy-induced neutropenia and thus treat or prevent infection in chemotherapy patients; Inhibit the growth of or to kill Mycobacterium Intracellular Avium Infection (MAC) |
| siRNA | Huntington, Alzheimers, Viral Infections (HIV, Hepatitis A, B or C, RSV), Cancers; Macular Degeneration |
| Prostaglandins | Hypertension |
| Cyclosporin | Transplant rejection; psoriasis, inflammatory alopecias; Sjogren's syndrome; Keratoconjunctivitis Sicca |
| Vasopressin | Nocturnal Enuresis; antidiuretic |
| Cromolyn sodium; | Asthma; allergies |
| Vancomycin | Treat or prevent antimicrobial-induced infections including, but not Emitted to methacillin-resistant Staphalococcus aureus and Staph. epidermiditis |
| gallium salts (such as gallium nitrate) | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of mycobacterium species, including but not limited to mycobacterium tubercolosis, and mycobacterium avium complex |

TABLE 2-continued

Active agent utilization

| Active Agent | Disease and Physiological Effect |
| --- | --- |
| Desferrioxamine (DFO) | Iron overload |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| BIBN4096BS - (1-Piperidinecarboxamide. N-[2-[[5-amino-1-[ [4-(4-pyridinyl)-l-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)]-) | Anti-migraine; calcitonin gene- related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| GLP-1, Exendin - 3, Exendin - 4, Obestatin | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| acyclovir | Used to treat herpes infections of the skin, lip and genitals; herpes zoster (shingles); and chickenpox |
| HIV Entry Inhibitors (e.g. Fuzeon) | Inhibit entry of HIV into host cells |
| Sumatriptin, almotriptan, naratriptan, rizatriptan, frovatriptan and eletriptan (piperidinyloxy)phenyl, (piperidinyloxy)pyridinyl, (piperidinylsulfanyl)phenyl and (piperidinylsulfanyl)pyridinyl compounds | anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | Antivirals |
| Peptide YY (PYY) and PYY-like Peptides (e.g. PYY[3-36]) | Obesity, Diabetes, Eating Disorders, Insulin-Resistance Syndromes |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternatively, the circulating levels of the active agent itself can be measured directly.

One embodiment of the present invention provides a pharmaceutical composition comprising an effective amount of insulin and an effective amount of at least one of the delivery agents described herein. For example, one embodiment of the present invention provides a pharmaceutical composition comprising about 50 to 800 mg/kg (e.g. 200 mg/kg) of insulin and about 0.1 to 2.0 mg/kg (e.g. 0.5 mg/kg) of any one of the delivery agent compounds of the present invention.

Yet another embodiment is method of treating diseases characterized by hyperglycemia, such as diabetes, comprising administering a pharmaceutical composition of the present invention to a subject.

One embodiment of the present invention provides a pharmaceutical composition comprising an effective amount of heparin and an effective amount of at least one of the delivery agents described herein. For example, one embodiment of the present invention provides a pharmaceutical composition comprising about 5 to 125 mg/kg (e.g. 25 mg/kg or 80 mg/kg) of heparin and about 5 to 500 mg/kg (e.g. 50 mg/kg or 200 mg/kg) of any one of the delivery agent compounds of the present invention.

Yet another embodiment is a method of treating or preventing disease characterized by intravascular thrombi by administering an effective amount of heparin and an effective amount of a delivery agent of the present invention to a subject.

Yet another embodiment is a method of preventing Deep Vain Thrombosis (DVT) in susceptible individuals by administering an effective amount of heparin and an effective amount of a delivery agent compound of the present invention to a subject.

One embodiment of the present invention provides a pharmaceutical composition comprising an effective amount of rhGH and an effective amount of at least one of the delivery agents described herein. For example, one embodiment of the present invention provides a pharmaceutical composition comprising about 0.25 to 10 mg/kg (e.g. 3 mg/kg) of rhGH and about 50 to 500 mg/kg (e.g. 200 mg/kg) of any one of the delivery agent compounds of the present invention.

Yet another embodiment is a method of treating or preventing short stature by administering an effective amount of rhGH and an effective amount of at least one delivery agent compound (formula I) of the present invention to a subject.

Yet another embodiment is method of treating or preventing a disease which requires supplementation of growth hormone by administering an effective amount of at least one delivery agent compound of the present invention to a subject.

One embodiment of the present invention provides a pharmaceutical composition comprising an effective amount of LHRH and an effective amount of at least one of the delivery agents described herein. For example, one embodiment of the present invention provides a pharmaceutical composition comprising about 0.1 to 10 mg/kg (e.g. 1 mg/kg) of LHRH and about 50-500 mg/kg (e.g. 200 mg/kg) of any one of the delivery agent compounds of the present invention.

Yet another embodiment is method of treating or preventing infertility in men or women which requires supplementation of LHRH by administering an effective amount of LHRH and an effective amount of at least one delivery agent of the present invention to a subject.

Yet another embodiment is method of treating or preventing a disease which requires supplementation of LHRH by administering an effective amount of LHRH and an effective amount of at least one delivery agent of the present invention to a subject.

One embodiment of the present invention provides a pharmaceutical composition comprising an effective amount of caspofungin acetate (e.g. Cancidas®) and an effective amount of at least one of the delivery agents described herein. For example, one embodiment of the present invention provides a pharmaceutical composition comprising about 5 to 125 mg/kg (e.g. 25 mg/kg) of caspofungin acetate and about 50 to 500 mg/kg (e.g. 200 mg/kg) of any one of the delivery agent compounds of the present invention.

Yet another embodiment is method of treating or preventing candidiasis or other systemic or localized fungal infections by administering an effective amount of caspofungin acetate and an effective amount of a delivery agent of the present invention to the subject.

EXAMPLES

The following examples illustrate the present invention without limitation.

Example 1—Preparation of
4-(4-Methoxyphenyl)butanoic acid (Compound 1)

A 500 mL round bottom flask equipped with a magnetic stirrer bar and an inert atmosphere (nitrogen gas) was charged with 5.25 mL (48.3 mmol) of anisole, 4.83 g (48.3 mmol) of succinic anhydride, 125 mL 1,1,2,2-tetrachloroethane and 125 mL of nitrobenzene. The reaction vessel was cooled with an external ice bath and stirred for 30 minutes. Aluminum trichloride (14.2 g, 106.4 mmol) was added to the pale yellow solution, which then turned to a dark reddish brown color. The ice bath was removed, and the reaction was allowed to stir at room temperature for 36 hours. Reaction was again cooled with an external ice bath. Prepared acidic solution by pouring 1N hydrogen chloride solution into a 100 mL beaker filled with ice. This solution was added to the reaction mixture carefully, drop-wise at first until reaction became clear with white precipitate. After that point a 10 mL portion was carefully added to test for reactivity, and then the remained of the ice/acid mixture was added. A second 100 mL of ice/acid mixture was added, the external ice bath removed and the pale emulsion was stirred for 2 hours. A white precipitate was collected form the emulsion by suction filtration. This solid was dissolved in 300 mL of 0.3 M sodium hydroxide, washed with 100 mL of ethyl acetate, and acidified to ~pH 1 with 1 M hydrochloric acid. The white precipitate that was collected upon vacuum filtration was washed with 3×100 mL de-ionized water, dried and reserved for use in next procedure.

To a 50 mL rounded bottom flask was added 4.77 g (86.1 mmol) of cut zinc. To this was added a solution of 0.22 g (0.81 mmol) of mercury(II)chloride and 0.2 mL concentrated hydrochloric acid (37%) in 4 mL of water. The mixture was allowed to stir at room temperature for 10 minutes. The liquid was decanted off and immediately replaced with a fresh solution of 10 mL concentrated hydrochloric acid (37%) in 2 mL of water. 3.00 g (14.4 mmol) of 4-(4-methoxyphenyl)-4-oxobutyric acid was added to the zinc mixture followed by an additional 10 mL of concentrated hydrochloric acid (37%) and 2 mL water. The reaction was heated to reflux for three hours, with an additional 0.4 mL of concentrated hydrochloric acid (37%) being added every thirty minutes. The reaction was cool to room temperature and allowed to mix overnight. 10 mL of diethyl ether was added to the reaction mixture and stirred for thirty minutes. The liquid was decanted away from the solid into a 125 mL separatory funnel and the solid residue was rinsed with 20 mL of ether which was also decanted into the separatory funnel. The aqueous layer was separated and extracted an additional two times with 30 mL diethyl ether. The combined organic layers were dried over sodium sulfate, filtered and solvent removed under reduced pressure. The residue solid was dissolved in ~250 mL of 0.3M sodium hydroxide solution and washed with 25 mL of ethyl acetate. The aqueous solution was acidified with ~200 mL 1N hydrochloric acid solution and allowed to rest overnight. The product (1.42 g, 51%) was isolated as a white solid, mp 57-58° C. Combustion analysis: Found: C, 67.87, H, 7.33%; $C_{11}H_{14}O_3$ requires C: 68.02, H: 7.27% 1H NMR (d6-DMSO): δ 12.0, s, 1H (COOH); δ 7.2 d, 2H (aryl H's); δ 6.8, d, 2H, (arylH's); δ 3.7, s, 3H (OMe H's); δ 2.5, t, 2H ($CH_2$ α to aryl group); δ 2.2, t, 2H ($CH_2$α to COOH), δ 1.75, p, 2H (middle $CH_2$).

Example 2—Preparation of 5-(2-Methoxyphenyl)pentanoic acid (Compound 2)

A 250 mL 3-neck round bottom flask equipped with a thermometer and a magnetic stirring bar was charged w/ 16.0 mL (18.1 g, 72.3 mmol) of triethyl 4-phosphocrotonate and 20 mL of tetrahydrofuran (THF). The clear solution was cooled to −78° C. in a dry ice/acetone bath and treated with 72.0 mL (72.0 mmol) of 1.0M lithium hexamethylsilizaide/THF solution, added slowly over 10 min. The red solution was stirred at −78° C. for 1 hour. One third of the anion solution was transferred via cannula to a solution of 3.28 g (24.1 mmol) of 2-anisaldehyde and 15 mL of THF. The reaction mixture warmed to 45° C. upon addition and was stirred at 25° C. for 20 hour. After dilution with 2:1 methyl t-butyl ether(MTBE)/hexanes, the reaction mixture was washed with water (4×40 mL) and brine (1×40 mL), dried over sodium sulfate, decolorized with silica gel and concentrated. The ethyl 5-(2-methoxyphenyl)pentadienoate was used as is.

A 500 mL Parr shaker reaction vessel was charged with the ethyl 5-(2-methoxyphenyl)pentadienoate isolated above and ethanol. This mixture was treated with 0.25 g of 10% palladium on charcoal and placed under an atmosphere of 45 psig of hydrogen gas in a Parr shaker apparatus. After hydrogen was no longer taken up, the reaction mixture was removed from the Parr shaker apparatus after dissipating the hydrogen gas, filtered through a Celite pad to remove the catalyst and concentrated to give crude ethyl 5-(2-methoxyphenyl)pentanoate.

A 125 mL Ehrlenmayer flask equipped with a magnetic stirrer bar was charged with the ethyl 5-(2-methoxyphenyl)pentanoate isolated above and ethanol. This solution was treated with 2N aqueous sodium hydroxide and heated to reflux. After 5 hr the clear solution was cooled to 25° C., washed with MTBE and acidified with aqueous 4% hydrochloric acid to give a red-orange solid which was isolated by filtration to give 3.44 g of 5-(2-methoxyphenyl)pentanoic acid. 1H NMR (d6-DMSO): δ 11.9, bs, 1H (COOH); δ 7.03, t, 1H, (arylH para to $CH_2$); δ 6.99, d, 1H (arylH ortho to $CH_2$); δ 6.80, d, 1H, (arylH ortho to OMe); δ 6.72, t, 1H (arylH para to OMe); δ 3.64, s, 3H ($OCH_3$); δ 2.41, t, 2H, ($CH_2$ α to aryl); δ 2.09, t, 2H ($CH_2$ α to COOH); δ 1.38, m, 4H ($CH_2$'s β to aryl and COOH). $^{13}C$ NMR (d6-DMSO): 174.42, 157.00, 129.77, 129.49, 127.04, 120.15, 110.56, 55.17, 33.53, 29.18, 28.87, 24.30.

Example 3—Preparation of 5-(3-Fluorophenyl)pentanoic acid (Compound 3)

A 250 mL 3-neck round bottom flask equipped with a thermometer and a magnetic stirring bar was charged w/ 16.0 mL (18.1 g, 72.3 mmol) of triethyl 4-phosphocrotonate and 20 mL of tetrahydrofuran (THF). The clear solution was cooled to −78° C. in a dry ice/acetone bath and treated with 72.0 mL (72.0 mmol) of 1.0M lithium hexamethylsilizaide/THF solution, added slowly over 10 min. The red solution was stirred at −78° C. for 1 hour. One third of the anion solution was transferred via cannula to a solution of 3.28 g (24.1 mmol) of 3-Fluorobenzaldehyde and 15 mL of THF. The reaction mixture warmed to 45° C. upon addition and was stirred at 25° C. for 20 hour. After dilution with 2:1 methyl t-butyl ether(MTBE)/hexanes, the reaction mixture was washed with water (4×40 mL) and brine (1×40 mL), dried over sodium sulfate, decolorized with silica gel and concentrated. The ethyl 5-(3-Fluorophenyl)pentadienoate was used as is.

A 500 mL Parr shaker reaction vessel was charged with the ethyl 5-(3-Fluorophenyl)pentadienoate isolated above and ethanol. This mixture was treated with 0.25 g of 10% palladium on charcoal and placed under an atmosphere of 45 psig of hydrogen gas in a Parr shaker apparatus. After hydrogen was no longer taken up, the reaction mixture was removed from the Parr shaker apparatus after dissipating the hydrogen gas, filtered through a Celite pad to remove the catalyst and concentrated to give crude ethyl 5-(3-Fluorophenyl)pentanoate.

A 125 mL Ehrlenmayer flask equipped with a magnetic stirrer bar was charged with the ethyl 5-(3-Fluorophenyl)pentanoate isolated above and ethanol. This solution was treated with 2N aqueous sodium hydroxide and heated to reflux. After 5 hr the clear solution was cooled to 25° C., washed with MTBE and acidified with aqueous 4% hydrochloric acid to give a red-orange solid which was isolated by filtration to give 3.44 g of 5-(3-Fluorophenyl)pentanoic acid. 1H NMR (d6-DMSO): δ 12.0, bs, 1H (COOH); δ 7.29, q, 1H, (arylH meta to F); δ 7.0, m, 3H (other arylH's); δ 2.57, t, 2H, ($CH_2$ α to aryl); δ 2.22, t, 2H ($CH_2$ α to COOH); δ 1.5, m, 4H ($CH_2$'s β to aryl and COOH). $^{13}C$ NMR (d6-DMSO): 174.35, 162.2 (d), 145.0, 130.0, 124.36, 114.8, 112.4, 34.37, 33.40, 30.02, 23.98.

Example 4—Preparation of 5-(3-Methoxyphenyl)pentanoic acid (Compound 4)

A 250 mL 3-neck round bottom flask equipped with a thermometer and a magnetic stirring bar was charged w/ 16.0 mL (18.1 g, 72.3 mmol) of triethyl 4-phosphocrotonate and 20 mL of tetrahydrofuran (THF). The clear solution was cooled to −78° C. in a dry ice/acetone bath and treated with 72.0 mL (72.0 mmol) of 1.0M lithium hexamethylsilizaide/THF solution, added slowly over 10 min. The red solution was stirred at −78° C. for 1 hour. One third of the anion solution was transferred via cannula to a solution of 3.28 g (24.1 mmol) of 3-anisaldehyde and 15 mL of THF. The reaction mixture warmed to 45° C. upon addition and was stirred at 25° C. for 20 hour. After dilution with 2:1 methyl t-butyl ether(MTBE)/hexanes, the reaction mixture was washed with water (4×40 mL) and brine (1×40 mL), dried over sodium sulfate, decolorized with silica gel and concentrated. The ethyl 5-(3-methoxyphenyl)pentadienoate was used as is.

A 500 mL Parr shaker reaction vessel was charged with the ethyl 5-(3-methoxyphenyl)pentadienoate isolated above and ethanol. This mixture was treated with 0.25 g of 10% palladium on charcoal and placed under an atmosphere of 45 psig of hydrogen gas in a Parr shaker apparatus. After hydrogen was no longer taken up, the reaction mixture was removed from the Parr shaker apparatus after dissipating the hydrogen gas, filtered through a Celite pad to remove the catalyst and concentrated to give crude ethyl 5-(3-methoxyphenyl)pentanoate.

A 125 mL Ehrlenmayer flask equipped with a magnetic stirrer bar was charged with the ethyl 5-(3-methoxyphenyl)pentanoate isolated above and ethanol. This solution was treated with 2N aqueous sodium hydroxide and heated to reflux. After 5 hr the clear solution was cooled to 25° C., washed with MTBE and acidified with aqueous 4% hydrochloric acid to give a red-orange solid which was isolated by filtration to give 3.44 g of 5-(3-methoxyphenyl)pentanoic acid.

1H NMR (d6-DMSO): δ 11.9, bs, 1H (COOH); δ 7.07, t, 1H, (arylH meta to OMe); δ 6.64, m, 3H (arylH's); δ 3.63, s, 3H (OCH$_3$); δ 2.44, t, 2H, (CH$_2$ α to aryl); δ 2.11, t, 2H (CH$_2$ α to COOH); δ 1.4, m, 4H (CH$_2$'s β to aryl and COOH). $^{13}$C NMR (d6-DMSO): 174.39, 159.23, 143.58, 129.18, 120.50, 113.89, 111.05, 54.83, 34.81, 33.46, 24.08.

Example 5—Preparation of 6-(3-Fluorophenyl) hexanoic acid (Compound 5)

A 250 mL 3-neck round bottom flask equipped with a thermometer and a magnetic stirring bar was charged w/ 6.02 g (13.6 mmol) of 4-carboxybutyltriphenylphosphonium bromide and 40 mL of tetrahydrofuran (THF). The slurry was cooled to −40° C. in a dry ice/acetone bath and treated with 28.5 mL (28.5 mmol) of 1.0M lithium hexamethylsilizaide/THF solution. The orange solution was allowed to warm to 25° C. The reaction mixture was cooled to −20° C. and treated with 1.40 mL (1.65 g, 13.3 mmol) of 3-fluorobenzaldehyde and then allowed to warm to 25° C. After 20 hour, the reaction mixture was diluted with methyl t-butyl ether (MTBE) and aqueous saturated sodium bicarbonate solution. The layers were separated. The aqueous phase was acidified with 4% aqueous hydrochloric acid to pH 2 and extracted with MTBE (1×40 mL). The organic phase was washed with brine (1×30 mL), dried over sodium sulfate and concentrated. The 6-(3-fluorophenyl)hex-5-enoic acid was used as is. A 500 mL Parr shaker reaction vessel was charged with the ethyl 6-(3-fluorophenyl)hex-5-enoic acid isolated above, 10 mL of ethylacetate and 30 mL of ethanol. This mixture was treated with 0.24 g of 10% palladium on charcoal and placed under an atmosphere of 58 psig of hydrogen gas in a Parr shaker apparatus. After hydrogen was no longer taken up, the reaction mixture was removed from the Parr shaker apparatus after dissipating the hydrogen gas, filtered through a Celite pad to remove the catalyst and concentrated to give crude 6-(3-fluorophenyl)hexanoic acid contaminated with triphenylphosphine oxide by-product. The product was taken up into MTBE and purified by extraction into aqueous saturated sodium bicarbonate solution (5×30 mL), acidification with 4% aqueous hydrochloric acid to pH 2 and extraction back into MTBE. The residual phosphine oxide was removed by adding 1 part hexanes to 2 parts MTBE and running through a plug of silica gel. The product was obtained after concentration to 1.37 g of 6-(3-fluorophenyl)hexanoic acid as a clear liquid. 1H NMR (d6-DMSO): δ 11.9, bs, 1H (COOH); δ 7.19, q, 1H, (arylH meta to F); δ 6.9, m, 3H (other arylH's); δ 2.47, t, 2H, (CH$_2$ α to aryl); δ 2.08, t, 2H (CH$_2$ α to COOH); δ 1.44, m, 4H (CH$_2$'s β to aryl and COOH); δ 1.17, p, 2H (CH$_2$ in middle of chain). $^{13}$C NMR (d6-DMSO): 174.42, 162.2 (d), 145.2, 130.0, 124.35, 114.9, 112.23, 34.61, 33.56, 30.33, 28.09, 24.25.

Example 6—Preparation of 3-(4-t-Butylphenyl)propanoic acid (Compound 6)

A 125 mL Ehrlenmayer flask equipped with a magnetic stirrer bar was charged with 7.76 g (47.8 mmol) of 4-t-butylbenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 4-t-butylcinnamic acid was isolated.

A 500 mL Parr shaker reaction vessel was charged with 3.10 g (15.2 mmol) of 4-t-butylcinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(4-t-butylphenyl)propanoic acid (3.07 g). 1H NMR (d6-DMSO): δ 12.2, bs, 1H (COOH); δ 7.16, d, 2H, (arylH's); δ 7.01, d, 2H (aryH's); δ 2.65, t, 2H, (CH$_2$ α to aryl); δ 2.38, t, 2H (CH$_2$ α to COOH); δ 1.13, s, 9H (t-Bu). $^{13}$C NMR (d6-DMSO): 174, 148, 137, 127.8, 125.9, 35, 33, 31.2, 29.5.

Example 7—Preparation of 3-(4-n-Butylphenyl)propanoic acid (Compound 7)

A 125 mL Ehrlenmayer flask equipped with a magnetic stirrer bar was charged with 7.76 g (47.8 mmol) of 4-n-butylbenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 4-n-butylcinnamic acid was isolated.

A 500 mL Parr shaker reaction vessel was charged with 3.10 g (15.2 mmol) of 4-n-butylcinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(4-n-butylphenyl)propanoic acid (3.07 g). 1H NMR (d6-DMSO): δ 12.0, bs, 1H (COOH); δ 7.00, d, 2H, (arylH's); δ 6.96, d, 2H (aryH's); δ 2.65, t, 2H, (CH$_2$ β to COOH); δ 2.39, m, 4H (CH$_2$ α to COOH and CH$_2$ α to aryl); δ 1.38, p, 2H (CH$_2$β to aryl); δ 1.16, hex, 2H (CH$_2$'s γ to aryl); δ 0.77, t, 3H (CH₃). ¹³C NMR (d6-DMSO): 173.79, 139.8, 137.98, 128.15, 128.03, 35.30, 34.40, 33.18, 29.94, 21.72, 13.74.

Example 8—Preparation of
3-(4-n-Propylphenyl)propanoic acid (Compound 8)

A 125 mL Ehrlenmayer flask equipped with a magnetic stirrer bar was charged with 7.76 g (47.8 mmol) of 4-n-propylbenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 4-n-Propylcinnamic acid was isolated.

A 500 mL Parr shaker reaction vessel was charged with 3.10 g (15.2 mmol) of 4-n-Propylcinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(4-n-Propylphenyl)propanoic acid (3.07 g). 1H NMR (d6-DMSO): δ 12.1, bs, 1H (COOH); δ 7.09, d, 2H, (arylH's); δ 7.05, d, 2H (arylH's); δ 2.75, t, 2H, (CH₂ β to COOH); δ 2.47, m, 4H (CH₂ α to COOH and CH₂ α to aryl); δ 1.52, hex, 2H (CH₂ β to aryl); δ 0.85, t, 3H (CH₃). ¹³C NMR (d6-DMSO): 173.76, 139.64, 138.01, 128.20, 128.02, 36.86, 35.28, 29.93, 24.11, 13.63.

Example 9—Preparation of
3-(4-n-Propoxyphenyl)propanoic acid (Compound 9)

A 125 mL Ehrlenmayer flask equipped with a magnetic stirrer bar was charged with 7.76 g (47.8 mmol) of 4-n-Propoxybenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 4-n-Propoxycinnamic acid was isolated.

A 500 mL Parr shaker reaction vessel was charged with 3.10 g (15.2 mmol) of 4-t-butylcinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(4-n-Propoxyphenyl)propanoic acid (3.07 g). 1H NMR (d6-DMSO): δ 12.0, bs, 1H (COOH); δ 7.00, d, 2H, (arylH's meta to O); δ 6.70, d, 2H (arylH's ortho to O); δ 3.76, t, 2H, (OCH₂); δ 2.63, t, 2H, (CH₂ α to aryl); δ 2.37, t, 2H (CH₂ α to COOH); δ 1.59, hex, 2H (CH₂ β to O); δ 0.85, t, 3H (CH₃). ¹³C NMR (d6-DMSO): 173.76, 156.97, 132.59, 129.13, 114.22, 68.81, 35.55, 29.48, 22.05, 10.38.

Example 10—Preparation of
3-(4-Isopropoxyphenyl)propanoic acid (Compound 10)

A 125 mL Ehrlenmayer flask equipped with a magnetic stirrer bar was charged with 7.76 g (47.8 mmol) of 4-Isopropoxybenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 4-Isopropoxycinnamic acid was isolated.

A 500 mL Parr shaker reaction vessel was charged with 3.10 g (15.2 mmol) of 4-t-butylcinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(4-4-Isopropoxyphenyl)propanoic acid (3.07 g). 1H NMR (d6-DMSO): δ 12.0, bs, 1H (COOH); δ 7.00, d, 2H, (arylH's meta to O); δ 6.70, d, 2H (arylH's ortho to O); δ 4.43, hept, 1H, (OCH); δ 2.63, t, 2H, (CH₂ α to aryl); δ 2.38, t, 2H (CH₂ α to COOH); δ 1.13, d, 6H (CH₃'s). ¹³C NMR (d6-DMSO): 173.78, 155.69, 132.50, 129.18, 115.44, 68.98, 35.50, 29.47, 21.85.

Example 11—Preparation of
3-(4-n-Butoxyphenyl)propanoic acid (Compound 11)

A 125 mL Ehrlenmayer flask equipped with a magnetic stirrer bar was charged with 7.76 g (47.8 mmol) of 4-n-Butoxybenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 4-n-Butoxycinnamic acid was isolated.

A 500 mL Parr shaker reaction vessel was charged with 3.10 g (15.2 mmol) of 4-n-Butoxycinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(4-n-Butoxyphenyl)propanoic acid (3.07 g). 1H NMR (d6-DMSO): δ 12.0, bs, 1H (COOH); δ 7.00, d, 2H, (arylH's meta to O); δ 6.70, d, 2H (arylH's ortho to O); δ 3.79, t, 2H, (OCH₂); δ 2.62, t, 2H, (CH₂ α to aryl); δ 2.35, t, 2H (CH₂ α to COOH); δ 1.55, p, 2H (CH₂ β to O); δ 1.30, hex, 2H (CH₂ β to COOH); δ 0.80, t, 3H (CH₃). ¹³C NMR (d6-DMSO): 173.77, 156.98, 132.58, 129.12, 114.21, 66.98, 35.56, 30.77, 29.48, 18.73, 13.67.

Example 12—Preparation of 3-(3-Phenoxyphenyl)propanoic acid (Compound 12)

A 125 mL Ehrlenmayer flask equipped with a magnetic stirrer bar was charged with 7.76 g (47.8 mmol) of 3-Phenoxybenzaldehyde, 5.28 g (50.7 mmol) of malonic acid and 2.2 mL (2.2 g, 27.2 mmol) of pyridine. The slurry was heated to 80° C., at which temperature a clear yellow solution formed. After stirring for 2 hr, the reaction mixture was cooled to 25° C. The resulting solid was isolated by filtration, rinsing with water (2×30 mL) and 2:1 methyl t-butyl ether (MTBE)/hexanes (2×30 mL). A total of 3.1 g of 3-Phenoxycinnamic acid was isolated.

A 500 mL Parr shaker reaction vessel was charged with 3.10 g (15.2 mmol) of 3-Phenoxycinnamic acid, 20 mL of ethyl acetate and 10 mL of ethanol. This mixture was treated with 0.15 g of 10% palladium on charcoal and placed under an atmosphere of 51 psig of hydrogen gas in a Parr shaker apparatus. A total of 14 psig of hydrogen was taken up in 16 hours. The reaction mixture was removed from the Parr shaker apparatus after dissipating the hydrogen gas, filtered through a Celite pad to remove the catalyst and concentrated to a white solid, 3-(3-Phenoxyphenyl)propanoic acid (3.07 g). 1H NMR (d6-DMSO): δ 12.1, bs, 1H (COOH); δ 7.37, t, 2H, (arylH's meta to O on unsubstituted phenyl); δ 7.27, t, 1H, (arylH meta to O on substituted phenyl); δ 7.12, t, 1H, (arylH para to O on unsubstituted phenyl); δ 6.99, m, 3H (arlyH's); δ 6.89, s, 1H (arylH ortho to both O and CH$_2$); δ 6.79, dd, 1H (arylH's ortho to O on substituted phenyl); δ 2.79, t, 2H, (CH$_2$ α to aryl); δ 2.51, t, 2H (CH$_2$ α to COOH). $^{13}$C NMR (d6-DMSO): 173.62, 156.65, 156.49, 143.22, 129.97, 129.80, 123.41, 123.27, 118.61, 118.44, 116.13, 34.98, 30.10.

Example 13—Preparation of 3-(3-Ethoxyphenyl)propanoic acid (Compound 13)

A 75 mL mini-block tube equipped with a magnetic stirrer bar was charged with 6.16 g (50.4 mmol) of 3-hydroxybenzaldehyde, 4.40 mL (8.58 g, 55.0 mmol) of ethyl iodide 30 mL of dimethylformamide and 6.05 g (57.1 mmol) of sodium carbonate. The slurry was heated to 50° C.

After 40 hours the reaction was only 50% complete so another 3 ml (5.85 g, 37.4 mmol) ethyl iodide was added. After 60 more hours another 3 mL (5.85 g, 37.4 mmol) ethyl iodide and 3 g (28.5 mmol) of sodium carbonate were added. The reaction mixture was cooled to 25° C. and diluted with methyl t-butyl ether (MTBE) and water. The organic layer was decanted off. The aqueous phase was rinsed with MTBE, again decanting off the organic layer. The combined organic layers were washed with 2N aqueous sodium hydroxide (3×30 mL) and brine (1×30 mL), dried over sodium sulfate and concentrated to give 3-ethoxybenzaldehyde which was used as (following the above procedure for 3-(4-t-butylphenyl)propanoic acid (Example 6) to prepare 3-(3-ethoxyphenyl)propanoic acid (1.31 g) as an off-white solid. 1H NMR (d6-DMSO): δ 12.0, bs, 1H (COOH); δ 7.04, t, 1H, (arylH meta to OEt); δ 6.6, m, 3H (other arylH's); δ 3.85, q, 2H, (OCH$_2$); 2.65, t, 2H, (CH$_2$ α to aryl); δ 2.39, t, 2H (CH$_2$ α to COOH); δ 1.18, t, 3H (CH$_3$). $^{13}$C NMR (d6-DMSO): 173.73, 158.49, 142.41, 129.25, 120.30, 114.40, 111.79, 62.72, 35.12, 30.35, 14.66.

Example 14—Preparation of 3-(3-Isopropoxyphenyl)propanoic acid (Compound 14)

A 75 mL mini-block tube equipped with a magnetic stirrer bar was charged with 6.16 g (50.4 mmol) of 3-hydroxybenzaldehyde, 4.40 mL (8.58 g, 55.0 mmol) of isopropyl iodide 30 mL of dimethylformamide and 6.05 g (57.1 mmol) of sodium carbonate. The slurry was heated to 50° C.

After 40 hours the reaction was only 50% complete so another 3 ml (5.85 g, 37.4 mmol) isopropyl iodide was added. After 60 more hours another 3 mL (5.85 g, 37.4 mmol) isopropyl iodide and 3 g (28.5 mmol) of sodium carbonate were added. The reaction mixture was cooled to 25° C. and diluted with methyl t-butyl ether (MTBE) and water. The organic layer was decanted off. The aqueous phase was rinsed with MTBE, again decanting off the organic layer. The combined organic layers were washed with 2N aqueous sodium hydroxide (3×30 mL) and brine (1×30 mL), dried over sodium sulfate and concentrated to give 3-Isopropoxybenzaldehyde which was used as (following the above procedure for 3-(4-t-butylphenyl)propanoic acid (Example 6) to prepare 3-(3-Isopropoxyphenyl)propanoic acid (1.31 g) as an off-white solid. 1H NMR (d6-DMSO): δ 12.0, bs, 1H (COOH); δ 7.03, t, 1H, (arylH meta to O-i-Pr); δ 6.6, m, 3H (other arylH's); δ 4.45, hept, 1H, (OCH); 2.65, t, 2H, (CH$_2$ α to aryl); δ 2.38, t, 2H (CH$_2$ α to COOH); δ 1.12, d, 6H (CH$_3$'s). $^{13}$C NMR (d6-DMSO): 173.70, 157.40, 142.46, 129.26, 120.17, 115.54, 112.93, 68.77, 35.09, 30.31, 21.84.

Example 15—Preparation of 3-(3-n-Butoxyphenyl)propanoic acid (Compound 15)

A 75 mL mini-block tube equipped with a magnetic stirrer bar was charged with 6.16 g (50.4 mmol) of 3-hydroxybenzaldehyde, 4.40 mL (8.58 g, 55.0 mmol) of n-butyl iodide 30 mL of dimethylformamide and 6.05 g (57.1 mmol) of sodium carbonate. The slurry was heated to 50° C.

After 40 hours the reaction was only 50% complete so another 3 ml (5.85 g, 37.4 mmol) n-butyl iodide was added. After 60 more hours another 3 mL (5.85 g, 37.4 mmol) n-butyl iodide and 3 g (28.5 mmol) of sodium carbonate were added. The reaction mixture was cooled to 25° C. and diluted with methyl t-butyl ether (MTBE) and water. The organic layer was decanted off. The aqueous phase was rinsed with MTBE, again decanting off the organic layer. The combined organic layers were washed with 2N aqueous sodium hydroxide (3×30 mL) and brine (1×30 mL), dried over sodium sulfate and concentrated to give 3-n-Butoxybenzaldehyde which was used as (following the above procedure for 3-(4-t-Butylphenyl)propanoic acid (Example 6) to prepare 3-(3-n-Butoxyphenyl)propanoic acid (1.31 g) as an off-white solid. 1H NMR (d6-DMSO): δ 12.0, bs, 1H (COOH); δ 7.04, t, 1H, (arylH meta to O-i-Pr); δ 6.6, m, 3H (other aryH's); δ 3.82, t, 2H, (OCH$_2$); 2.65, t, 2H, (CH$_2$ α to aryl); δ 2.38, t, 2H (CH$_2$ α to COOH); δ 1.56, p, 2H (CH$_2$ β to O); δ 1.30, hex, 2H (CH$_2$ β to COOH); δ 0.81, t, 3H (CH$_3$). $^{13}$C NMR (d6-DMSO): 173.75, 158.69, 142.44, 129.23, 120.28, 114.40, 111.84, 66.87, 35.15, 30.78, 30.36, 18.74, 13.68.

Example 16—Preparation of 3-(3-n-Propoxyphenyl)propanoic acid (Compound 16)

A 75 mL mini-block tube equipped with a magnetic stirrer bar was charged with 6.16 g (50.4 mmol) of 3-hydroxybenzaldehyde, 4.40 mL (8.58 g, 55.0 mmol) of n-propyl iodide 30 mL of dimethylformamide and 6.05 g (57.1 mmol) of sodium carbonate. The slurry was heated to 50° C.

After 40 hours the reaction was only 50% complete so another 3 ml (5.85 g, 37.4 mmol) n-propyl iodide was added. After 60 more hours another 3 mL (5.85 g, 37.4 mmol) n-propyl iodide and 3 g (28.5 mmol) of sodium carbonate were added. The reaction mixture was cooled to 25° C. and diluted with methyl t-butyl ether (MTBE) and water. The organic layer was decanted off. The aqueous phase was rinsed with MTBE, again decanting off the organic layer. The combined organic layers were washed with 2N aqueous sodium hydroxide (3×30 mL) and brine (1×30 mL), dried over sodium sulfate and concentrated to give 3-n-Propylbenzaldehyde which was used as (following the above procedure for 3-(4-t-butylphenyl)propanoic acid (Example 6) to prepare 3-(3-n-Propylphenyl)propanoic acid (1.31 g) as an off-white solid. 1H NMR (d6-DMSO): δ 12.0, bs, 1H (COOH); δ 7.04, t, 1H, (arylH meta to O-i-Pr); δ 6.6, m, 3H (other aryH's); δ 3.77, t, 2H, (OCH$_2$); 2.66, t, 2H, (CH$_2$ α to aryl); δ 2.39, t, 2H (CH$_2$ α to COOH); δ 1.59, hex, 2H (CH$_2$ β to O); δ 0.85, t, 3H (CH$_3$). $^{13}$C NMR (d6-DMSO): 173.74, 158.67, 142.42, 129.25, 120.29, 114.42, 111.85, 68.68, 35.12, 30.34, 22.05, 10.40.

Example 17—Preparation of 3-(3-Isobutoxyphenyl)propanoic acid (Compound 17)

A 75 mL mini-block tube equipped with a magnetic stirrer bar was charged with 6.16 g (50.4 mmol) of 3-hydroxybenzaldehyde, 4.40 mL (8.58 g, 55.0 mmol) of isobutyl iodide 30 mL of dimethylformamide and 6.05 g (57.1 mmol) of sodium carbonate. The slurry was heated to 50° C.

After 40 hours the reaction was only 50% complete so another 3 ml (5.85 g, 37.4 mmol) isobutyl iodide was added. After 60 more hours another 3 mL (5.85 g, 37.4 mmol) isobutyl iodide and 3 g (28.5 mmol) of sodium carbonate were added. The reaction mixture was cooled to 25° C. and diluted with methyl t-butyl ether (MTBE) and water. The organic layer was decanted off. The aqueous phase was rinsed with MTBE, again decanting off the organic layer. The combined organic layers were washed with 2N aqueous sodium hydroxide (3×30 mL) and brine (1×30 mL), dried over sodium sulfate and concentrated to give 3-Isobutoxybenzaldehyde which was used as (following the above procedure for 3-(4-t-butylphenyl)propanoic acid (Example 6) to prepare 3-(3-Isobutoxyphenyl)propanoic acid (1.31 g) as an off-white solid. 1H NMR (d6-DMSO): δ 12.0, bs, 1H (COOH); δ 7.03, t, 1H, (arylH meta to O-i-Pr); δ 6.6, m, 3H (other aryH's); δ 3.59, d, 2H, (OCH$_2$); 2.65, t, 2H, (CH$_2$ α to aryl); δ 2.38, t, 2H (CH$_2$ α to COOH); δ 1.86, n, 1H, (CH); δ 0.84, d, 6H (CH$_3$'s). $^{13}$C NMR (d6-DMSO): 173.74, 158.78, 142.43, 129.24, 120.31, 114.42, 111.92, 73.53, 35.13, 30.35, 27.71, 19.06.

Example 18—Preparation of 3-(4-Isobutoxyphenyl)propanoic acid (Compound 18)

A 75 mL mini-block tube equipped with a magnetic stirrer bar was charged with 6.16 g (50.4 mmol) of 4-hydroxybenzaldehyde, 4.40 mL (8.58 g, 55.0 mmol) of isobutyl iodide 30 mL of dimethylformamide and 6.05 g (57.1 mmol) of sodium carbonate. The slurry was heated to 50° C.

After 40 hours the reaction was only 50% complete so another 3 ml (5.85 g, 37.4 mmol) isobutyl iodide was added. After 60 more hours another 3 mL (5.85 g, 37.4 mmol) isobutyl iodide and 3 g (28.5 mmol) of sodium carbonate were added. The reaction mixture was cooled to 25° C. and diluted with methyl t-butyl ether (MTBE) and water. The organic layer was decanted off. The aqueous phase was rinsed with MTBE, again decanting off the organic layer. The combined organic layers were washed with 2N aqueous sodium hydroxide (3×30 mL) and brine (1×30 mL), dried over sodium sulfate and concentrated to give 4-Isobutoxybenzaldehyde which was used as (following the above procedure for 3-(4-t-butylphenyl)propanoic acid (Example 6) to prepare 3-(4-Isobutoxyphenyl)propanoic acid (1.31 g) as an off-white solid. 1H NMR (d6-DMSO): δ 12.0, bs, 1H (COOH); δ 7.00, d, 2H, (arylH's meta to O); δ 6.70, d, 2H (arylH's ortho to O); δ 3.60, d, 2H, (OCH$_2$); 2.65, t, 2H, (CH$_2$ α to aryl); δ 2.38, t, 2H (CH$_2$ α to COOH); δ 1.89, n, 1H, (CH); δ 0.87, d, 6H (CH$_3$'s). $^{13}$C NMR (d6-DMSO): 173.76, 157.06, 132.61, 129.12, 114.26, 73.67, 35.56, 29.47, 27.68, 19.04.

Example 19—Preparation of 4-(4-Ethylphenyl)butanoic acid (Compound 19)

A 250 mL 3-neck round bottom flask equipped with a thermometer and a magnetic stirring bar was charged with 4.01 g (61.3 mmol) of zinc dust and 35 mL of dimethylformamide (DMF) under a nitrogen atmosphere. The slurry was treated with 0.56 g (2.2 mmol) of iodine. The red disappeared in 90 seconds. The reaction mixture was treated with 6.00 mL (8.18 g, 42.0 mmol) of ethyl 4-bromobutyrate and heated to 80° C. for 4 hour. The reaction mixture was cooled to 30° C. and treated with 4.98 g (21.5 mmol) of 4-iodoethylbenzene and 0.48 g (0.9 mmol) of dichlorobis(triphenylphosphine)nickel(II). The reaction mixture was heated to 45° C. for 80 hours. The cooled reaction mixture was treated with aqueous 4% hydrochloric acid to quench the excess zinc. The mixture was extracted with methyl t-butyl ether (MTBE) (1×60 mL). The organic phase was washed with brine (1×30 mL), dried over sodium sulfate and concentrated. The crude ethyl 4-(4-ethylphenyl)butyrate was taken up in ethanol, treated with 20 mL of 2N aqueous sodium hydroxide, and heated to reflux. After 4 hours the reaction mixture was cooled to 25° C. and washed with MTBE (2×30 mL). The aqueous phase was acidified with aqueous 4% hydrochloric acid. A solid was isolated by filtration to give 1.99 g of 4-(4-ethylphenyl)butanoic acid. 1H NMR (d6-DMSO): δ 11.9, bs, 1H (COOH); δ 6.98, d, 2H, (arylH's); δ 6.95, d, 2H (aryH's); δ 2.41, m, 4H, (CH$_2$'s α to aryl); δ 2.07, t, 2H (CH$_2$ α to COOH); δ 1.64, m, 2H (CH$_2$ β to both aryl and COOH); δ 1.03, t, 3H (CH$_3$). $^{13}$C NMR (d6-DMSO): 174.23, 141.08, 138.67, 128.20, 127.65, 33.97, 33.03, 27.73, 26.35, 15.65.

Example 20—Preparation of 4-(4-Isopropylphenyl)butanoic acid (Compound 20)

A 250 mL 3-neck round bottom flask equipped with a thermometer and a magnetic stirring bar was charged with 4.01 g (61.3 mmol) of zinc dust and 35 mL of dimethylformamide (DMF) under a nitrogen atmosphere. The slurry was treated with 0.56 g (2.2 mmol) of iodine. The red disappeared in 90 seconds. The reaction mixture was treated with 6.00 mL (8.18 g, 42.0 mmol) of ethyl 4-bromobutyrate and heated to 80° C. for 4 hour. The reaction mixture was cooled to 30° C. and treated with 4.98 g (21.5 mmol) of 4-iodoisopropylbenzene and 0.48 g (0.9 mmol) of dichlorobis (triphenylphosphine)nickel(II). The reaction mixture was heated to 45° C. for 80 hours. The cooled reaction mixture was treated with aqueous 4% hydrochloric acid to quench the excess zinc. The mixture was extracted with methyl t-butyl ether (MTBE) (1×60 mL). The organic phase was washed with brine (1×30 mL), dried over sodium sulfate and concentrated. The crude ethyl 4-(4-Isopropylphenyl)butyrate was taken up in ethanol, treated with 20 mL of 2N aqueous sodium hydroxide, and heated to reflux. After 4 hours the reaction mixture was cooled to 25° C. and washed with MTBE (2×30 mL). The aqueous phase was acidified with aqueous 4% hydrochloric acid. A solid was isolated by filtration to give 1.99 g of 4-(4-Isopropylphenyl)butanoic acid. 1H NMR (d6-DMSO): δ 11.9, bs, 1H (COOH); δ 7.01, d, 2H, (arylH's); δ 6.96, d, 2H (aryH's); δ 2.70, hept, 1H, (CH) δ 2.40, t, 2H, (CH$_2$ α to aryl); δ 2.07, t, 2H (CH$_2$ α to COOH); δ 1.63, p, 2H (CH$_2$ β to both aryl and COOH); δ 1.04, d, 6H (CH$_3$'s). $^{13}$C NMR (d6-DMSO): 174.23, 145.75, 138.81, 128.18, 126.15, 33.97, 33.07, 32.99, 26.33, 23.93.

Example 21—Preparation of 5-(4-Ethylphenyl)pentanoic acid (Compound 21)

A 250 mL 3-neck round bottom flask equipped with a thermometer and a magnetic stirring bar was charged with 4.01 g (61.3 mmol) of zinc dust and 35 mL of dimethylformamide (DMF) under a nitrogen atmosphere. The slurry was treated with 0.56 g (2.2 mmol) of iodine. The red disappeared in 90 seconds. The reaction mixture was treated with 6.00 mL (8.18 g, 42.0 mmol) of ethyl 4-bromopentanoate and heated to 80° C. for 4 hour. The reaction mixture was cooled to 30° C. and treated with 4.98 g (21.5 mmol) of 4-iodoethylbenzene and 0.48 g (0.9 mmol) of dichlorobis(triphenylphosphine)nickel(II). The reaction mixture was heated to 45° C. for 80 hours. The cooled reaction mixture was treated with aqueous 4% hydrochloric acid to quench the excess zinc. The mixture was extracted with methyl t-butyl ether (MTBE) (1×60 mL). The organic phase was washed with brine (1×30 mL), dried over sodium sulfate and concentrated. The crude ethyl 4-(4-ethylphenyl)pentanoate was taken up in ethanol, treated with 20 mL of 2N aqueous sodium hydroxide, and heated to reflux. After 4 hours the reaction mixture was cooled to 25° C. and washed with MTBE (2×30 mL). The aqueous phase was acidified with aqueous 4% hydrochloric acid. A solid was isolated by filtration to give 1.99 g of 4-(4-ethylphenyl)pentanoic acid. 1H NMR (d6-DMSO): δ 11.9, bs, 1H (COOH); δ 6.98, d, 2H, (arylH's); δ 6.95, d, 2H (aryH's); δ 2.42, m, 4H, (CH$_2$'s α to aryl); δ 2.09, t, 2H (CH$_2$ α to COOH); δ 1.4, m, 2H (CH$_2$'s β to aryl and COOH); δ 1.03, t, 3H (CH$_3$). $^{13}$C NMR (d6-DMSO): 174.38, 140.90, 139.11, 128.15, 127.57, 34.39, 33.49, 30.45, 27.73, 24.09, 15.66.

Example 22—Oral Delivery of Insulin to Male Sprague-Dawley Rats

Insulin stock solution (15 mg/ml) (Human zinc insulin, Calbiochem-Novabiochem Corp., La Jolla, Calif.) was prepared with deionized water. Oral dosing compositions containing 200 mg/kg of delivery agent compound and 0.5 mg/kg of insulin in aqueous solution were prepared with the delivery agent compound shown in Table 3 below. Either the sodium salt of the delivery agent compound was used or the free acid was converted to the sodium salt with one equivalent of sodium hydroxide.

The dosing solution was administered to fasted male Sprague-Dawley rats by oral gavage with an average weight of about 225-250 grams. Blood glucose levels were then determined by glucometer (One Touch Ultra®, LifeScan, Inc.) and compared to vehicle control (1 ml/kg of water). Samples were collected prior to dosing (time 0) and at 15, 30, 45 and 60 minutes after dosing. The % glucose reduction values in Table 3 are values found at the C minimum, and are an average % reduction with respect to the number of times the experiment was run for each delivery agent.

TABLE 3

Percent Change in Glucose after delivery agent & insulin administration
Insulin
200 mg/kg Delivery Agent Compound; 0.5 mg/kg Insulin

| Delivery Agent Compound | % Glucose Reduction | Delivery Agent Compound | % Glucose Reduction |
|---|---|---|---|
| 1 | −43.6 | 36 | −16.0 |
| 3 | −6.6 | 37 | −13.8 |
| 4 | −38.3 | 38 | −54.6 |
| 5 | −12.3 | 38 | −24.0 |
| 6 | −50.4 | 39 | −63.3 |
| 6 | −59.8 | 39 | −39.5 |
| 6 | −47.4 | 39 | −31.6 |
| 6 | −53.1 | 40 | −40.8 |
| 7 | −8.9 | 41 | −43.9 |
| 8 | −6.2 | 41 | −33.3 |
| 9 | −30.5 | 42 | −36.5 |
| 9 | −25.8 | 43 | −24.1 |
| 10 | −49.4 | 44 | −53.4 |
| 10 | −61.7 | 44 | −34.6 |
| 11 | −8.5 | 44 | −33.3 |
| 12 | −24.8 | 45 | −12.2 |
| 13 | −40.2 | 46 | −12.0 |
| 14 | −42.9 | 47 | −29.2 |
| 15 | −8.5 | 48 | −2.4 |
| 16 | −22.1 | 49 | −32.0 |
| 17 | −12.6 | 50 | −46.1 |
| 18 | −43.6 | 50 | −42.9 |
| 19 | −31.0 | 51 | −29.3 |
| 20 | −23.2 | 52 | −18.2 |
| 21 | −14.6 | 53 | −50.6 |
| 23 | −13.6 | 53 | −35.5 |
| 25 | −53.8 | 53 | −56.9 |
| 25 | −45.3 | 54 | −18.0 |
| 25 | −34.2 | 55 | −45.2 |
| 25 | −20.2 | 55 | −42.7 |
| 26 | −6.6 | 55 | −36.0 |
| 27 | −10.8 | 55 | −48.4 |
| 27 | −10.8 | 56 | −21.8 |
| 28 | −57.3 | 57 | −26.5 |
| 28 | −50.2 | 58 | −40.2 |
| 28 | −53.7 | 59 | −52.0 |
| 28 | −53.8 | 59 | −31.2 |
| 28 | −39.2 | 60 | −36.7 |
| 29 | −22.5 | 61 | −41.0 |
| 32 | −13.8 | 61 | −20.5 |
| 33 | −20.9 | 62 | −20.5 |
| 33 | −22.7 | 62 | −26.4 |
| 34 | −27.2 | 63 | −4.5 |
| 35 | −18.2 | 63 | −13 |
| 64 | −45.5 | 69 | 13.1 |
| 64 | −29.6 | 70 | −5.5 |
| 65 | −30.7 | 71 | −14.1 |
| 66 | −19.5 | 72 | −13.1 |
| 67 | −8.6 | 73 | −37.3 |
| 68 | −36.1 | | |

The invention claimed is:

1. A composition comprising:

(A) at least one biologically active agent; and (B) at least one delivery agent compound represented by formula I

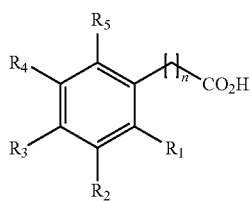

Formula I or a pharmaceutically acceptable salt thereof, wherein
n is 1-12,
and $R_1$-$R_5$ are independently hydrogen, $C_1$-$C_6$, alkyl, $C_2$-$C_4$ alkenyl, halogen, $C_1$-$C_4$ alkoxy, hydroxyl, $C_6$-$C_{14}$ aryloxy, or $C_1$-$C_6$ alkylhalo group,
with the proviso that at least one of $R_1$-$R_5$ is methyl, $C_1$-$C_4$ alkoxy, hydroxyl or halogen.

2. The composition of claim 1, wherein the delivery agent is selected from 4-(4-methoxyphenyl)butanoic acid, 5-(2-methoxyphenyl)pentanoic acid, 5-(3-fluorophenyl)pentanoic acid, 5-(3-methoxyphenyl)pentanoic acid, 6-(3-fluorophenyl)hexanoic acid, 3-(4-n-propoxyphenyl)propanoic acid, 3-(4-isopropoxyphenyl)propanoic acid, 3-(4-n-butoxyphenyl)propanoic acid, 3-(3-phenoxyphenyl)propanoic acid, 3-(3-ethoxyphenyl)propanoic acid, 3-(3-isopropoxyphenyl) propanoic acid, 3-(3-n-butoxyphenyl)propanoic acid, 3-(3-n-propoxyphenyl)propanoic acid, 3-(3-isobutoxyphenyl) propanoic acid, 3-(4-isobutoxyphenyl)propanoic acid, or pharmaceutically acceptable salts thereof.

3. The composition of claim 1, wherein the delivery agent is conjugated to a polymer by a linkage group selected from the group consisting of —NHC(O)NH—, —C(O)NH—, —NHC(O)—; —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond.

4. The composition of claim 1, wherein the biologically active agent is a protein, polypeptide, peptide, hormone, polysaccharide, mucopolysaccharide, carbohydrate, lipid, or combination thereof.

5. The composition of claim 1, wherein the biologically active agent is selected from the group consisting of: argatroban, BIBN-4096BS, growth hormones, human growth hormones recombinant human growth hormones (rhGH), bovine growth hormones, porcine growth hormones, growth hormone releasing hormones, growth hormone releasing factor, glucagon, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolyn sodium, sodium chromoglycate, disodium chromoglycate, vancomycin, desferrioxamine (DFO), parathyroid hormone (PTH), fragments of PTH, glucagon-like peptide 1 (GLP-1), antimicrobials, anti-fungal agents, vitamins; analogs, fragments, mimetics and polyethylene glycol (PEG)-modified derivatives of these compounds; gallium or gallium salts; glucagons; zanamivir, sumatriptan, almotriptan, naratriptan, rizatriptan, frovatriptan, eletriptan, caspofungin acetate, CPHPC, siRNA and any combination thereof.

6. The composition of claim 1, further comprising at least one enzyme inhibitor.

7. The composition of claim 1, wherein the weight ratio of delivery agent to active agent ranges from about 800:1 to about 10:1.

8. A method of preparing pharmaceutical composition, comprising mixing at least one delivery agent compound of claim 1, and a biologically active agent.

9. A dosage unit form comprising:
(A) a delivery agent according to claim 1; and
(B) a biologically active agent; and
(C) (a) an excipient,
(b) a diluent,
(c) a disintegrant,
(d) a lubricant,
(e) a plasticizer,
(f) a colorant,
(g) an enzyme inhibitor
(h) a dosing vehicle, or
(i) any combination thereof.

10. The dosage unit form of claim 9, wherein the biologically active agent comprises at least one protein, polypeptide, peptide, hormone, polysaccharide, mucopolysaccharide, carbohydrate, or lipid.

11. The dosage unit form of claim 10, wherein the biologically active agent is selected from the group consisting of: argatroban, BIBN-4096BS, growth hormones, human growth hormones (hGH), recombinant human growth hormones (rhGH), bovine growth hormones, porcine growth hormones, growth hormone releasing hormones, growth hormone releasing factor, interferons, glucagon, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolyn sodium, sodium chromoglycate, disodium chromoglycate, vancomycin, desferrioxamine, parathyroid hormone, fragments of PTH, glucagon-like peptide 1 (GLP-1), antimicrobials, anti-fungal agents, vitamins; analogs, fragments, mimetics and polyethylene glycol-modified derivatives of these compounds; gallium or gallium salts; glucagons, zanamivir, sumatriptan, almotriptan, naratriptan, rizatriptan, frovatriptan, eletriptan, capsofungin acetate, CPHPC, SiRNA and any combination thereof.

12. A method for administering a biologically-active agent to an animal in need of the agent, the method comprising administering orally to the animal the composition of claim 1.

13. A method for administering a biologically-active agent to an animal in need of the agent, the method comprising administering orally to the animal the dosage unit form of claim 9.

14. A method for administering a biologically-active agent to an animal in need of the agent, the method comprising administering to the animal the composition of claim 1 intranasally, sublingually, intraduodenally, subcutaneously, buccally, intracolonicly, rectally, vaginally, mucosally, pulmonary, transdermally, intradermally, parenterally, intravenously, intramuscularly, via the ocular system, or by traversing the blood-brain barrier.

15. A method for administering a biologically-active agent to an animal in need of the agent, the method comprising administering to the animal the dosage unit of claim 9 intranasally, sublingually, intraduodenally, subcutaneously, buccally, intracolonicly, rectally, vaginally, mucosally, pulmonary, transdermally, intradermally, parenterally, intravenously, intramuscularly, via the ocular system, or by traversing the blood-brain barrier.

16. A method for administering a biologically active agent comprising administering a delivery agent compound of claim 1, followed by administration of a biologically active agent.

17. The method of claim 16, wherein the biologically active agent is a protein, polypeptide, peptide, hormone, polysaccharide, mucopolysaccharide, carbohydrate, or lipid.

18. A method for increasing the bioavailability of a biologically active agent comprising administering to an animal a composition of claim 1.

19. A method for preparing a composition comprising mixing:

(A) at least one active agent;

(B) at least one delivery agent compound of claim 1;

(C) optionally, an enzyme inhibitor; and (D) optionally, a dosing vehicle.

20. A compound selected from the group consisting of 4-(4-methoxyphenyl)butanoic acid, 5-(2-methoxyphenyl)pentanoic acid, 5-(3-fluorophenyl)pentanoic acid, 5-(3-methoxyphenyl)pentanoic acid, 6-(3-fluorophenyl)hexanoic acid, 3-(4-t-butylphenyl) propanoic acid, 3-(4-n-butylphenyl)propanoic acid, 3-(4-n-propylphenyl)propanoic acid, 3-(4-n-propoxyphenyl)propanoic acid, 3-(4-isopropoxyphenyl)propanoic acid, 3-(4-n-butoxyphenyl)propanoic acid, 3-(3-phenoxyphenyl)propanoic acid, 3-(3-ethoxyphenyl)propanoic acid, 3-(3-isopropoxyphenyl)propanoic acid, 3-(3-n-butoxyphenyl)propanoic acid, 3-(3-n-propoxyphenyl)propanoic acid, 3-(3-isobutoxyphenyl)propanoic acid, 3-(4-isobutoxyphenyl)propanoic acid, 4-(4-ethylphenyl)butanoic acid, 4-(4-isopropylphenyl)butanoic acid, and 5-(4-ethylphenyl)pentanoic acid, or pharmaceutically acceptable salts thereof.

* * * * *